United States Patent [19]

Lapidus

[11] Patent Number: 4,583,986

[45] Date of Patent: Apr. 22, 1986

[54] CATALYZED BISMUTH DYE SYSTEM FOR HUMAN HAIR

[75] Inventor: Herbert Lapidus, Ridgefield, Conn.

[73] Assignee: Combe Incorporated, White Plains, N.Y.

[21] Appl. No.: 320,927

[22] Filed: Nov. 13, 1981

Related U.S. Application Data

[63] Continuation of Ser. No. 285,026, Jul. 20, 1981, abandoned.

[51] Int. Cl.$^4$ .............................................. A61K 7/13
[52] U.S. Cl. .................................... 8/405; 8/425; 8/435
[58] Field of Search ............... 8/405, 404, 574, 576, 8/577, 578, 425, 435

[56] References Cited

U.S. PATENT DOCUMENTS

| | | | |
|---|---|---|---|
| 2,888,313 | 5/1959 | Mautner | 8/574 |
| 2,960,443 | 11/1960 | Rosmarin | 8/435 |
| 3,075,821 | 1/1963 | Goldemberg et al. | 8/404 |
| 3,153,563 | 10/1964 | Warner et al. | 8/578 |
| 3,410,648 | 11/1968 | Mautner et al. | 8/574 |
| 3,954,393 | 5/1976 | Lapidus | 8/405 |
| 3,989,452 | 11/1976 | Hugelshofer | 8/576 |
| 4,195,972 | 4/1980 | Lapidus | 8/405 |
| 4,306,873 | 12/1981 | Lapidus | 8/405 |
| 4,310,329 | 1/1982 | Holland | 8/404 |

FOREIGN PATENT DOCUMENTS

| | | | |
|---|---|---|---|
| 245098 | 12/1925 | United Kingdom | 8/576 |
| 815738 | 7/1959 | United Kingdom | 8/576 |

OTHER PUBLICATIONS

Gleason et al., *Clinical Toxicology of Commercial Products*, 3rd ed., The Williams & Wilkins Co., Baltimore, 1969, p. 59.

*Primary Examiner*—Albert T. Meyers
*Assistant Examiner*—John M. Kilcoyne
*Attorney, Agent, or Firm*—Roland T. Bryan

[57] ABSTRACT

A dyeing system for human hair is provided comprising a bismuth salt and a catalyst which has a chemical structure having either an oxygen atom possessing a resonating double bond or an oxygen atom of an ether group attached to a carbon atom, such catalyst being characterized by a high degree of solubility in water and having a molecular weight of from about 50 to about 170.

12 Claims, No Drawings

CATALYZED BISMUTH DYE SYSTEM FOR HUMAN HAIR

CROSS REFERENCED TO RELATED APPLICATION

This application is a continuation-in-part of applicant's co-pending application Ser. No. 285,026, filed July 20, 1981, now abandoned.

This invention provides for a novel system for dyeing human hair comprising a bismuth salt and a catalyst component in admixture with a composition comprising triethanolamine, at least one sulfur containing component, Triton X 100, and water.

BACKGROUND OF THE INVENTION

In the cosmetic industry, dyestuffs have been employed in various forms primarily for the coloration of human hair. In such applications, numerous limitations have been placed upon the dye systems employed based upon considerations mandated by concern for human safety and the need to avoid exposure to substances having high toxicity, as well as other adverse effects which may result to the user's skin or hair tissue.

Bismuth containing dyeing systems have heretofore been employed for use in the coloration of human hair, particularly for applications involving the darkening of graying hair either in men or women.

In applications involving bismuth containing dyeing systems, a variety of different additives and enhancers have been suggested to improve the effect achieved. Numerous mechanisms of dyeing and dye formations have been put forth in this art.

In spite of the long history of the dyeing art, a completely satisfactory dyeing system for human hair has yet to be achieved. Amongst the drawbacks of various known hair dyeing systems are the relatively poor level of coloration imparted to the hair subjected to dyeing, and/or the relative efficiency and ease with which the dye is imparted to the hair fibers to achieve the desired coloration.

While a considerable degree of effort has been expended in seeking to achieve improved dyeing systems for human hair, in general, the known means of enhancing the basic hair dyeing process have only met with limited success.

Such means as have been developed, while helpful in improving one or more perceived inadequacies of a given dyeing system, often render the remaining characteristics of such systems more troublesome, or do nothing to improve similar aspects in other dyeing systems which have also been used for human hair.

Exemplary of the state of the art as to various known systems for dyeing human hair and related materials are the following:

U.S. Pat. No. 2,185,467, which issued on Jan. 2, 1940, to Kritchevsky, discloses the use of formamide or derivatives thereof with organic dyes to enchance the adhesion of such dyes to human hair. No mention is made of the use of bismuth containing dyes nor the advantages to be achieved utilizing the catalysts of the present invention with such dyeing systems.

U.S. Pat. No. 2,983,651, which issued on May 9, 1961, to Seemuller, relates to the dyeing of animal fibers involving the use of a solution of a direct dye in an aqueous organic solvent which is chemically indifferent with respect to the dye and to the product to be dyed. Although a number of dyeing systems are defined as applicable utilizing the disclosed invention, no mention is made of the use of a bismuth containing dyeing system such as that which is the subject of the instant application.

U.S. Pat. No. 3,075,821, which issued on Jan. 29, 1963, discloses the use of a two-step process for dyeing a keratinous material involving the application of metal salt such as that of cobalt, nickel, copper, zinc, palladium, silver, cadmium, or mixtures thereof in aqueous solution and the subsequent treatment of the keratinous fibers in a solution of dithio-oxamide. No disclosure is made of the use of a bismuth containing dyeing system such as that disclosed in the instant application.

U.S. Pat. No. 3,206,363, which issued on Sept. 14, 1965, to Lecher, et al., is directed to use of certain alkyl derivatives of urea in dyeing systems utilized for dyeing either natural or synthetic polyamide fibers, including living human hair, in order to prevent the staining of the scalp and/or scalp irritation which was attendant upon the use of various other art employed solvents. No teaching is apparent as to the use of a bismuth containing dye system having the enhanced characteristics displayed by the compositions of the present invention.

U.S. Pat. No. 3,402,986, which issued on Sept. 24, 1968, to Zviak, et al., relates to a method of dyeing hair at ambient temperature using a direct dye dispersed in a aqueous medium containing not more than 10% by weight of a water miscible alcohol selected from the group of alcohols which are colorless, non-toxic and chemically indifferent to the dye and the hair.

U.S. Pat. No. 3,632,290, which issued on Jan. 4, 1972, to Tucker is directed to a composition for the dyeing of human hair involving the use of mixtures of aryl and alkyl glycol eithers in aqueous media as carriers and solubilizers for normally water-insoluble dyes involving a broad range of dyestuffs. No specific teaching is apparent as to the bismuth containing dye system disclosed in the present application.

U.S. Pat. No. 3,822,112, which issued on July 2, 1974, to Zviak, et al., is directed to a method of dyeing human hair which comprises applying a hair dye composition comprising an aqueous solution of a direct dye which can be either an azo dye, a basic dye or a nitro dye in combination with from 0.5 to 8% by weight of 2-phenoxyethanol and 3.5 to 12% by weight of ethyl glycol acetate. Again, no mention is made of the use of a bismuth containing dye system such as that which is the subject of the instant application, nor of the use of the subject catalyst components disclosed herein.

None of the foregoing prior art teachings suggest the subject dyeing system or the method which is the subject of the instant application, which involves the utilization of a bismuth salt and a catalyst having the specific characteristics set forth in order to achieve a highly desirable increase in the efficacy of such a dye system when employed in the treatment of human hair.

It is, therefore, an object of the present invention to provide for a dyeing system for human hair comprising a bismuth salt and a catalyst component which achieves a substantial improvement in the efficacy in the coloration of human hair subjected to such a dyeing system, as compared with similar hair dyeing systems of the prior art.

It is a further object of the present invention to provide for a method of dyeing human hair comprising a bismuth salt and a catalyst component which will achieve a desired degree of coloration in the subject hair in a shorter period of time than has been heretofore possible utilizing similar such bismuth containing dyeing systems of the prior art.

These and other objects of th present invention will become apparent from the following description of the invention.

SUMMARY OF THE INVENTION

In accordance with the present invention, a dyeing system for human hair is provided comprising a bismuth salt and a catalyst which has a chemical structure having either an oxygen atom possessing a resonating double bond or an oxygen atom of an ether group attached to a carbon atom, such catalyst being characterized by a high degree of solubility in water and having a molecular weight of from about 50 to about 170.

This invention provides for a novel dyeing system for human hair comprising a bismuth salt and a catalyst component in admixture with a composition comprising triethanolamine, at least one sulfur containing component, Triton X 100, and water.

DESCRIPTION OF THE INVENTION

It has been found that in the utilization of bismuth containing dyeing systems in order to impart coloration to human hair, the incorporation of a catalyst component which has a chemical structure havng either an oxygen atom possessing a resonating double bond or an oxygen atom of an ether group attached to a carbon atom, such catalyst being characterized by a high degree of solubility in water and having a molecular weight of from about 50 to about 170, will serve to greatly enhance the resultant degree of coloration achieved and to shorten the time in which it takes to reach a desired degree of coloration in a given hair sample.

Normally, various bismuth salts, such as, bismuth citrate which are not soluble in aqueous solution, are employed in hair dyeing compositions such as those of the present invention, along with various other components, including sulfur and sodium thiosulfate, as well as triethanolamine and a commercially procurable wetting agent such as Triton X 100 (a commercially available wetting agent from Rohm & Hass), in order to form a composition which provides the necessary availability of sulfur ions as well as bismuth ions in solution for ultimate disposition in the form of a bismuth sulfide on the hair which is being treated.

The sulfides of bismuth are normally quite insoluble in aqueous media, thus rendering it difficult for its ions to penetrate the hair fiber and form a molecular sulfide of bismuth therein, thereby imparting the necessary degree of coloration. Such molecular sulfides of bismuth which are in fact deposited on the treated hair will generally be in the form of bismuth sulfide (mono), which has a molecular weight of 241.07 and would impart a grayish color to the hair, or bismuth trisulfide which has a molecular weight of 514.20 and would impart a brownish-black coloration to the hair.

It is hypothesized that the catalyst component described hereinbefore provides a convenient means whereby the negative oxygen of the catalyst may attract the positive bismuth ion and the positive carbon of the catalyst may attract the negative sulfur ion.

After penetration of the hair fiber and subsequent exsiccation, the attracted ions will unite to form the colored bismuth sulfide or trisulfide component within the hair fiber.

It has been found that the ability of human hair to be effectively colored by a bismuth containing dyeing system involves a complex interaction of a number of components in the dyeing system and requires the presence of an excess of sulfur ions in order to provide the necessary sulfur for the formation of bismuth sulfide or trisulfide in the hair fibers.

The catalyst component which possesses a chemical structure having either an oxygen atom possessing a resonating double bond or an oxygen atom of an ether group attached to a carbon atom, such catalyst being characterized by a high degree of solubility in water and having a molecular weight of from about 50 to about 170, may be selected from the group comprising n-methyl-2-pyrrolidone, n-cyclohexyl-2-pyrrolidone, butyrolactone, CARBITOL (diethylene glycol monoethyl ether) 1,4-dioxane, tetrahydrofuran, and other such similar components having the recited chemical structure, high degree of solubility in water and molecular weight range.

It has been found that one may achieve significant improvement in the coloration imparted to human hair utilizing a basic composition comprising a soluble bismuth salt dyeing system and from about 0.5 to about 20 weight percent of a catalyst component as described hereinbefore. Preferably about 10 weight percent based upon the total weight of the hair dyeing composition will be employed in order to achieve optimum results.

The nature of the present invention may be more clearly understood by recourse to the following examples which are set forth for illustrative purposes only and are not to be held as limiting the invention thereto.

EXAMPLES

General Comments

In carrying out the following Examples to illustrate the effectiveness of the preferred compositions of the present invention, the following basic composition was employed.

TABLE 1

| BASIC COMPOSITION | |
| --- | --- |
| COMPONENT | WEIGHT PERCENT |
| Bismuth Citrate | 0.50 |
| Triethanolamine (TEA) | 1.00 |
| Sulfur (ppt.) | 0.50 |
| Sodium thiosulfate (5.0 $H_2O$) | 0.50 |
| Triton X 100 (wetting agent) | 0.10 |
| Water, deionized | 87.40 |
| Catalyst Component | 10.00 |
| | 100.00 |

The hair dyeing compositions of the following Examples were prepared as follows:

Initially, 50% of the water was heated to 70° C., to which the TEA and bismuth citrate was added with continuous mixing. At this point, a blue or purple haze appeared. Mixing was continued until solution occured with no sign of dispersed powder.

The mixture was cooled to 40° C. and the sodium thiosulfate added with continuous mixing.

In a separate container the sulfur and Triton X 100 were dispersed in 10% of the water until a slurry was achieved. The slurry was then ground for about twenty minutes to insure that no sulfur lumps were evident.

The ground slurry was added to the mixture of bismuth citrate, TEA and sodium thiosulfate with continuous mixing, and the remaining water used to rinse the slurry container and the rinse water added to the mixture.

The catalyst component was then added to the rest of the mixture with further mixing.

The resultant hair dyeing compositions were applied to various samples of human hair for a period of one minute and then allowed to dry.

The coloration of the hair samples twenty four (24) hours later after dyeing were visually evaluated and rated on a scale of 1 to 10, wth 1 being representative of the results achieved using no catalyst component in the basic composition of Table 1 and 10 being optimum effectiveness. The Twenty four hour wait for color comparison is due to the gradual darkening that occurred with example XX.

EXAMPLES I–XII

Various hair samples were treated with hair dyeing systems having the basic composition set forth in Table 1, with no catalyst component, and with 10% by weight of various other components to illustrate their relative effectiveness as catalysts in the hair dyeing system of the present invention.

Table 2 sets forth the various catalyst components attempted and the relative color rating, on a scale of 1 to 10, achieved utilizing the aforementioned procedures where the dyed samples are compared with the control twenty four (24) hours after dyeing the sample.

TABLE 2
EXAMPLES I–XII

| EXAMPLE NO. | CATALYST COMPONENT | 24 HOUR RATING |
|---|---|---|
| I | None (control) | 1 |
| II | N—methyl-2-pyrrolidone (M—pyrol) | 10 |
| III | N—cyclohexyl-2-pyrrolidone | 10 |
| IV | Butyrolactone | 8 |
| V | CARBITOL (diethylene glycol monoethyl ether) | 8 |
| VI | 1,4-Dioxane | 5 |
| VII | Tetrahydrofuran | 5 |
| VIII | Butanediol* | 1 |
| IX | Hexylene glycol* | 1 |
| X | Isopropyl alcohol* | 1 |
| XI | Benzyl alcohol (4% sol.)* | 1 |
| XII | Butanol (7.9% sol.)* | 1 |

*Indicates no activity as a catalyst in the system of the present invention.

EXAMPLES XIII–XVII

In order to demonstrate the criticality of various aspects of the hair dyeing system of the present invention, a number of formulations of dyeing compositions were prepared and evaluated in accordance with the aforementioned procedures.

The compositions of each and the relative rating obtained after applying each to samples of human hair to be treated are set forth in Table 3.

TABLE 3
EXAMPLES XIII–XVII
Example No. (Weight % of Each Component)

| COMPONENT | XIII | XIV | XV | XVI | XVII |
|---|---|---|---|---|---|
| Bismuth Citrate | 0.5 | 0.5 | — | 0.5 | 0.5 |
| Triethanolamine | 1.0 | 1.0 | 1.0 | 1.0 | 1.0 |
| Sulfur, ppt. | 0.5 | — | 0.5 | — | 0.5 |
| Sodium Thiosulfate | 0.5 | — | — | 0.5 | 0.5 |
| Triton X 100 | 0.1 | 0.1 | 0.1 | 0.1 | 0.1 |
| Water | 87.4 | 88.4 | 87.9 | 87.9 | 87.4 |
| Urea | 10.0 | — | — | — | — |
| M—pyrol | — | 10.0 | 10.0 | 10.0 | 10.0 |
| Lead Acetate | — | — | 0.5 | — | — |
| 24 HOUR RATING (1 to 10) | 1 | 1 | 1 | 3 | 10 |

These results illustrate that a catalyst component such as urea having a carbonyl attached to a nitrogen atom is ineffective in the dyeing system of the present invention. Similarly, the presence of elemental sulfur in the system is critical to the effective formation of bismuth sulfides. Further, the use of other heavy metal salts, such as lead acetate is also shown to be ineffective, thus, rendering the useful catalyst components, advantageous with bismuth salts, but not with lead salts.

EXAMPLES XVIII–XXXVII

In order to illustrate the range of the amount of catalyst component to be employed in the bismuth salt dyeing system of the composition set forth in Table 1, a number of formulations were prepared based upon the basic composition varying only the weight percent of the specific catalyst component utilized with the remainder being water to comprise one hundred percent. These formulations were each prepared and evaluated in accordance with the procedures set forth above.

The catalyst component, weight percents utilized and relative color rating on a scale of 1 to 10 are set forth in Tables 4, 5 and 6.

TABLE 4
EXAMPLES XVIII–XXVI
Catalyst Component - M—pyrol

| EXAMPLE NO. | WEIGHT PERCENT CATALYST | RATING | 24 HOUR RATING |
|---|---|---|---|
| XVIII | 0.5 | 1 | 3 |
| XVIX | 1.0 | 1 | 3 |
| XX | 2.5 | 1 | 3 |
| XXI | 3.0 | 5 | 5 |
| XXII | 5.0 | 8 | 8 |
| XXIII | 7.5 | 10 | 10 |
| XXIV | 10.0 | 10 | 10 |
| XXV | 20 | 10 | 10 |
| XXVI | 30 | 10 | 10 |

TABLE 5
EXAMPLES XXVII–XXXII
Catalyst Component - CARBITOL (diethylene glycol monoethyl ether)

| EXAMPLE NO. | WEIGHT PERCENT CATALYST | 24 HOUR RATING |
|---|---|---|
| XXVII | 1.0 | 1 |
| XXVIII | 2.5 | 1 |
| XXIX | 5.0 | 5 |
| XXX | 7.5 | 5 |
| XXXI | 20 | 8 |
| XXXII | 30 | 8 |

TABLE 6
EXAMPLES XXXIII–XXXVIII
Catalyst Component - Butyrolactone

| EXAMPLE NO. | WEIGHT PERCENT CATALYST | 24 HOUR RATING |
|---|---|---|
| XXXIII | 1 | 1 |
| XXXIV | 2.5 | 1 |
| XXXV | 5.0 | 5 |

TABLE 6-continued

EXAMPLES XXXIII-XXXVIII
Catalyst Component - Butyrolactone

| EXAMPLE NO. | WEIGHT PERCENT CATALYST | 24 HOUR RATING |
|---|---|---|
| XXXVI | 7.5 | 5 |
| XXXVII | 20.0 | 8 |
| XXXVIII | 30.0 | 8 |

While the formulations utilized for the above examples employed both elemental sulfur and sodium thiosulfate, it is contemplated that elemental sulfur alone, other thiosulfates such as potassium thiosulfate and combinations thereof will also serve to provide the necessary sulfur ions for the method of the present invention to be effective.

Similarly, while TEA has been employed as a complexing agent, other similar complexing agents including ammonia (NH8+) can also be effectively employed.

While the invention has been described with reference to a number of embodiments, it will be apparent to one skilled in the art that there are additional numerous variations which properly fall within the range of this invention. Therefore, it should be understood that the foregoing embodiments and examples are set forth to illustrate the advantages which may be achieved utilizing the present invention and should not be interpreted as limiting the scope of the invention.

We claim:

1. A composition for dyeing human hair comprising bismuth citrate, elemental sulfur, a thiosulphate selected from the group consisting of sodium thiosulphate and potassium thiosulphate, a complexing agent selected from the group consisting of triethanolamine and ammonia, a catalyst and usual additives and processing aids, where said catalyst is of a chemical structure having either an oxygen atom possessing a resonating double bond or an oxygen atom of an ether group attached to a carbon atom said catalyst having a high degree of solubility in water and a molecular weight from about 50-170.

2. A composition for dyeing human hair comprising about 0.50 weight percent of bismuth citrate, in admixture with about 1.00 weight percent triethanolamine, about 0.50 weight percent sulfur, about 0.50 weight percent sodium thiosulate, about 0.10 weight percent Triton X 100, about 87.40 weight percent water and about 10 weight percent of a catalyst component.

3. A composition according to claim 1, wherein the catalyst component is selected from the group comprising N-methyl-2-pyrrolidone, N-cyclohexyl-2-pyrrolidone, butyrolactone, CARBITOL, 1,4-dioxan and tetrahydrofuran.

4. A composition according to claim 1 wherein the catalyst component is present in an amount from about 0.5 to about 20.0 weight percent and the water is present in an amount from about 77.40 to about 96.90 weight percent based upon the total weight of the composition.

5. A composition according to claim 2, wherein the catalyst component is N-methyl-2-pyrrolidone.

6. A composition according to claim 2, wherein the catalyst component is N-cyclohexyl-2-pyrrolidone.

7. A composition according to claim 2, wherein the catalyst component is butyrolactone.

8. A composition according to claim 2, wherein the catalyst component is CARBITOL.

9. A composition according to claim 2, wherein the catalyst component is 1,4-dioxane.

10. A composition according to claim 2, wherein the catalyst component is tetrahydrofuran.

11. A dyeing composition according to claim 4 wherein the catalyst is present in an amount of about 10 weight percent based upon the total weight of composition.

12. A dyeing composition according to claim 3 wherein there is a wetting agent Triton X 100.

* * * * *